United States Patent
Zhang et al.

(10) Patent No.: US 11,684,789 B2
(45) Date of Patent: Jun. 27, 2023

(54) BIOSTIMULATOR HEADER ASSEMBLY HAVING CERAMIC HELIX MOUNT

(71) Applicant: Pacesetter, Inc., Sylmar, CA (US)

(72) Inventors: Bei Ning Zhang, Pasadena, CA (US); Brett C. Villavicencio, Valencia, CA (US); Perry Li, Arcadia, CA (US)

(73) Assignee: PACESETTER, INC., Sylmar, CA (US)

( * ) Notice: Subject to any disclaimer, the term of this patent is extended or adjusted under 35 U.S.C. 154(b) by 60 days.

(21) Appl. No.: 17/158,903

(22) Filed: Jan. 26, 2021

(65) Prior Publication Data
US 2021/0228888 A1 Jul. 29, 2021

Related U.S. Application Data

(60) Provisional application No. 62/966,455, filed on Jan. 27, 2020.

(51) Int. Cl.
*A61N 1/375* (2006.01)
*A61N 1/05* (2006.01)

(52) U.S. Cl.
CPC .......... *A61N 1/3756* (2013.01); *A61N 1/0573* (2013.01); *A61N 1/3754* (2013.01); *A61N 1/37512* (2017.08)

(58) Field of Classification Search
CPC ............... A61N 1/3756; A61N 1/0573; A61N 1/37512; A61N 1/3754; A61N 1/3752; A61N 1/375
See application file for complete search history.

(56) References Cited

U.S. PATENT DOCUMENTS

| | | | |
|---|---|---|---|
| 2016/0008594 A1* | 1/2016 | Régnier | B23P 19/04 219/121.64 |
| 2017/0165494 A1* | 6/2017 | Kronmueller | H05K 5/0247 |
| 2019/0083800 A1* | 3/2019 | Yang | A61N 1/368 |
| 2019/0134413 A1* | 5/2019 | Mar | A61N 1/37512 |
| 2019/0232066 A1* | 8/2019 | Lim | A61N 1/37512 |
| 2020/0129763 A1* | 4/2020 | Paspa | A61N 1/37205 |

* cited by examiner

*Primary Examiner* — Gary Jackson
*Assistant Examiner* — Alexander M Eisenberg
(74) *Attorney, Agent, or Firm* — Womble Bond Dickinson (US) LLP

(57) ABSTRACT

A biostimulator, such as a leadless pacemaker, including a header assembly having an electrical feedthrough assembly incorporating a helix mount, is described. The header assembly includes a fixation element mounted on the helix mount. The helix mount is mounted on a flange of the electrical feedthrough assembly, and thus, the fixation element can attach the leadless biostimulator to a target tissue. An electrode of the electrical feedthrough assembly is mounted within the flange to deliver a pacing impulse to the target tissue. A ceramic portion of the helix mount is disposed between the flange and the electrode to block an electrical path between the electrode and the flange. Accordingly, the helix mount both retains the fixation element on the leadless biostimulator and electrically isolates the flange and electrode components of the electrical feedthrough. Other embodiments are also described and claimed.

25 Claims, 8 Drawing Sheets

BIOSTIMULATOR HEADER ASSEMBLY HAVING CERAMIC HELIX MOUNT

This application claims the benefit of priority of U.S. Provisional Patent Application No. 62/966,455, filed on Jan. 27, 2020, which is incorporated herein by reference in its entirety to provide continuity of disclosure.

BACKGROUND

Field

The present disclosure relates to biostimulators having header assemblies. More specifically, the present disclosure relates to leadless biostimulators having header assemblies that include an electrical feedthrough assembly, and methods of manufacturing such header assemblies.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. The pulse generator usually connects to the proximal end of one or more implanted leads through a feedthrough assembly, which creates an isolated electrical pass-through into a hermetic case for pulse/sense transmissions to a target tissue. The feedthrough assembly can be used in low voltage or high voltage applications. A distal end of the implanted leads, which typically have lengths of 50 to 70 centimeters, contains one or more electrodes for positioning adjacent to the inside or outside wall of a cardiac chamber. The leads have an insulated electrical conductor or conductors for connecting the pulse generator to the electrodes in the heart. Accordingly, the pulse generator can deliver a pacing pulse from within a hermetically sealed housing through the feedthrough assembly, the lead, and the electrode to the target tissue.

Conventional pacemakers have several drawbacks, including a risk of lead or feedthrough assembly breakage, complex connections between the leads and the feedthrough assembly, and a risk of infection and morbidity due to the separate leads and pulse generator components. Many of the issues associated with conventional pacemakers are resolved by the development of a self-contained and self-sustainable biostimulator, or so-called leadless biostimulator. The leadless biostimulator can be attached to tissue within a dynamic environment, e.g., within a chamber of a beating heart, to deliver pacing pulses directly to the tissue without the use of leads.

SUMMARY

Existing leadless biostimulators have a hermetically sealed device package containing internal components to generate and receive electrical pulses through an electrode of an electrical feedthrough to or from a target tissue. The electrical feedthrough creates an isolated electrical pass-through from the hermetic case for pulse/sense transmissions to the target tissue. The electrical feedthrough typically includes the electrode and a flange to connect the electrical feedthrough to a housing of the device package. The electrical feedthrough also includes an insulator and a gasket to electrically isolate the flange from the electrode. The flange, the insulator, and the electrode are brazed to form a hermetic seal between the components.

The device package of existing leadless biostimulators may also include a helix mount that is fastened to the electrical feedthrough assembly by a threaded connection. The helix mount supports a fixation element, such as a fixation helix, that can be screwed into the target tissue to attach the device to the target tissue. Typically, the helix mount and the electrical feedthrough assembly are separate components. For example, the helix mount retains the fixation helix and does not serve an electrical isolation function. Instead, the electrical feedthrough assembly incorporates the insulator and the gasket for that purpose.

The insulator and the gasket of existing leadless biostimulators are additional components, having respective costs and assembly complexities, as well as presenting potential electrical or mechanical failure pathways. Furthermore, the separation of the helix mount and the electrical feedthrough of existing leadless biostimulators requires threaded connections that are manufacturing intensive and present a potential mechanical failure pathway. Accordingly, existing leadless biostimulators can benefit from a header assembly that includes fewer and/or less costly manufacturing processes and components to reduce cost and increase mechanical stability and electrical reliability.

A leadless biostimulator having a header assembly including a helix mount integrated in an electrical feedthrough assembly is described. In an embodiment, the header assembly includes a flange, an electrode, and a helix mount. The electrode is disposed within a flange channel of the flange. The helix mount includes a ceramic portion between the flange and the electrode. For example, the ceramic portion can be radially between the flange and the electrode. Accordingly, a shortest path between the flange and the electrode may intersect the ceramic portion of the helix mount, and the ceramic portion can electrically isolate the flange from the electrode.

The ceramic portion of the helix mount can include an annular section extending from a proximal end of the helix mount to a distal end of the helix mount. For example, a mount bore can extend through the helix mount from the proximal end to the distal end, and the annular section can extend around the mount bore. The electrode can be disposed within the mount bore, and thus, isolated by the annular section.

In an embodiment, the flange is coupled to the helix mount by a threadless connector. The flange can include a flange connector that connects to a mount connector of the helix mount. For example, the flange connector and mount connector can have mating channels and prongs. The channels can receive the prongs to allow the flange to be fastened to the helix mount using a simple twisting operation, without the manufacturing intensive operations of alignment and multiple rotations required by threaded connectors.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of implementations of the present disclosure are set forth with particularity in the claims that follow. A better understanding of the features and advantages of such implementations will be obtained by reference to the following detailed description that sets forth illustrative examples in which the principles of the disclosure are utilized, and the accompanying drawings of which:

DETAILED DESCRIPTION

Figure 1:
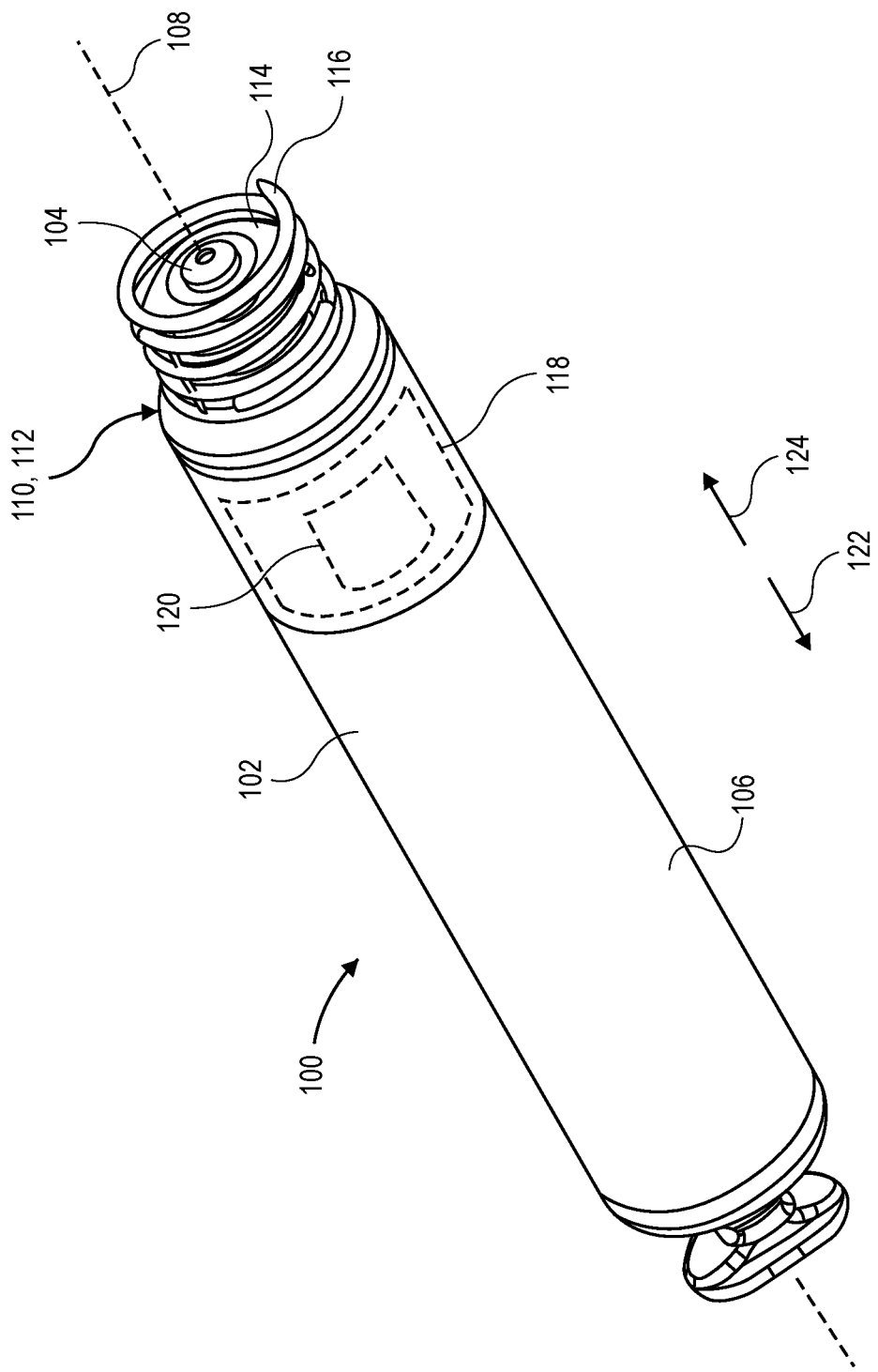
FIG. 1 is a perspective view of a leadless biostimulator, in accordance with an embodiment.

Implementations of the present disclosure include a biostimulator, e.g., a leadless cardiac pacemaker, having a header assembly that includes an electrical feedthrough assembly incorporating a helix mount. The biostimulator may be used to pace cardiac tissue, e.g., in the ventricles or the atria of a heart. The biostimulator may be used in other applications, however, such as deep brain stimulation. Thus, reference to the biostimulator as being a cardiac pacemaker is not limiting.

Descriptions of various implementations of the present disclosure are made with reference to the figures. However, certain implementations may be practiced without one or more of these specific details, or in combination with other known methods and configurations. In the following description, numerous specific details are set forth, such as specific configurations, dimensions, and processes, in order to provide a thorough understanding of the example implementations. In other instances, well-known processes and manufacturing techniques have not been described in particular detail in order to not unnecessarily obscure the description. Reference throughout this specification to "one implementation," "an implementation," or the like, means that a particular feature, structure, configuration, or characteristic described is included in at least one implementation. Thus, the appearance of the phrase "one implementation," "an implementation," or the like, in various places throughout this specification are not necessarily referring to the same implementation. Furthermore, the particular features, structures, configurations, or characteristics may be combined in any suitable manner in one or more implementations.

The use of relative terms throughout the description may denote a relative position or direction. For example, "distal" may indicate a first direction along a longitudinal axis of a biostimulator. Similarly, "proximal" may indicate a second direction opposite to the first direction. Such terms are provided to establish relative frames of reference, however, and are not intended to limit the use or orientation of a biostimulator to a specific configuration described in the various implementations below.

In an aspect of the present disclosure, a leadless biostimulator including a header assembly including an electrical feedthrough assembly incorporating a helix mount. The integrated helix mount provides good mechanical and electrical performance of the electrical feedthrough assembly using few parts. The helix mount and a flange of the electrical feedthrough assembly can have threadless connectors that make assembly of the components easy and repeatable. The helix mount can be joined directly to the flange and an electrode of the electrical feedthrough assembly by a filler metal, and thus, the electrical feedthrough assembly can have a mechanically stable and hermetic electrical pass-through without the need for additional insulator or gasket components. The helix mount may include a ceramic portion disposed between the flange and the electrode, and thus, the helix mount may provide electrical isolation between the flange and the electrode. Accordingly, the header assembly of the leadless biostimulator uses few parts and a cost-effective manufacturing process to achieve robust mechanical stability and reliable electrical performance.

Referring to FIG. 1, a perspective view of a leadless biostimulator is shown in accordance with an embodiment. A biostimulator 100 can be a leadless biostimulator, e.g., a leadless cardiac pacemaker used to deliver pacing impulses to the atria or ventricles of a heart. The biostimulator 100 can include a housing 102 having electrodes. For example, the biostimulator 100 includes each of a distal electrode 104 and a proximal electrode 106 disposed on or integrated into the housing 102. The distal electrode 104 and the proximal electrode 106 can be used to sense and pace the heart. The electrodes 104 can be integral to the housing 102 or connected to the housing 102, e.g., at a distance of less than several centimeters from the housing.

In an embodiment, the housing 102 contains an energy source (not shown) to provide power to the pacing electrodes 104. The energy source can be, for example, a battery, such as a lithium carbon monofluoride (CFx) cell, or a hybrid battery, such as a combined CFx and silver vanadium oxide (SVO/CFx) mixed-chemistry cell. Similarly, the energy source can be an ultracapacitor. In one implementation, the energy source can be an energy harvesting device, such as a piezoelectric device that converts mechanical strain into electrical current or voltage. The energy source can also be an ultrasound transmitter that uses ultrasound technology to transfer energy from an ultrasound subcutaneous pulse generator to a receiver-electrode implanted on an endocardial wall.

The housing 102 can have a longitudinal axis 108, which may be an axis of symmetry along which several other biostimulator components are disposed. For example, a header assembly 110 can be mounted on a distal end of the housing 102 along the longitudinal axis 108. The header assembly 110 can include an electrical feedthrough assembly 112, incorporating a helix mount 114 as described below, and a fixation element 116 mounted on the helix mount 114. The assembled components of the header assembly 110 can provide a distal region of the biostimulator 100 that attaches to the target tissue, e.g., via engagement of the fixation element 116 with the target tissue. The distal region can deliver a pacing impulse to the target tissue, e.g., via the distal electrode 104 that is held against the target tissue.

The housing 102 can have an electronics compartment 118 (shown by hidden lines). More particularly, the electronics compartment 118 can be a cavity laterally surrounded by a housing wall, e.g., a cylindrical wall, extending around the longitudinal axis 108. The housing wall can include a conductive, biocompatible, inert, and anodically safe material such as titanium, 316L stainless steel, or other similar materials, to laterally enclose the electronics compartment 118 between the energy source of the biostimulator 100 within a proximal portion of the housing 102, and the header assembly 110 at the distal portion of the biostimulator 100. More particularly, an energy source container can proximally enclose the electronics compartment 118 and the electrical feedthrough assembly 112 can distally enclose the electronics compartment 118. The electrical feedthrough assembly 112, the housing wall, and the power source container can surround a volume of the electronics compartment 118.

Figure 2:
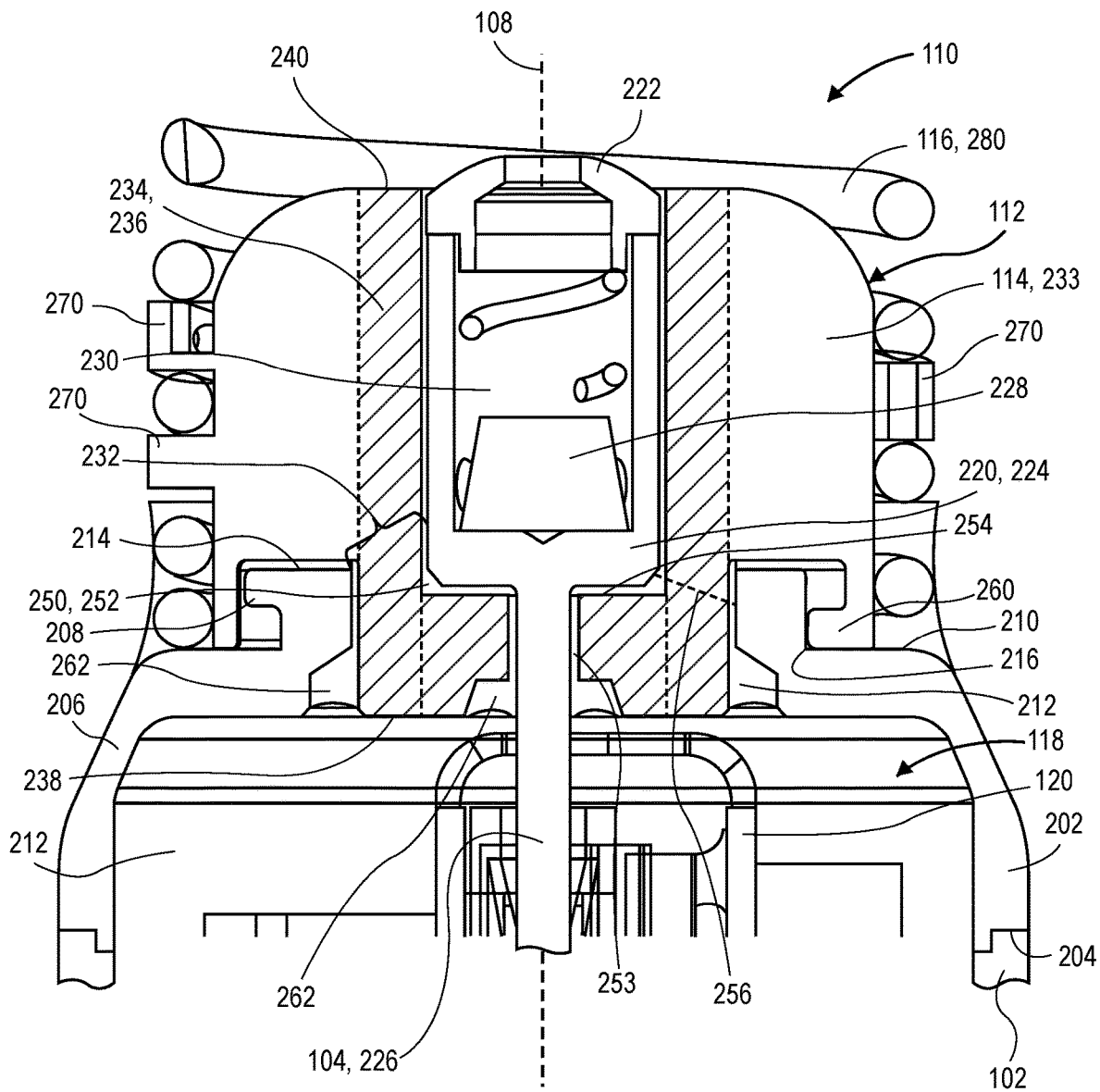
FIG. 2 is a sectional view of a header assembly mounted on a housing of a leadless biostimulator, in accordance with an embodiment.

In one implementation, the electronics compartment 118 contains an electronics assembly 120 (shown by hidden lines). The electronics assembly 120 can be mounted in the electronics compartment 118. For example, the electronics assembly 120 can include, without limitation, a flexible circuit or a printed circuit board having electrical connectors that connect to electrical pins of the electrical feedthrough assembly 112 and the energy source. FIG. 2 illustrates an example of an electrical connector (a socket connector) receiving an electrode pin of the distal electrode 104. The electronics assembly 120 has one or more electronic components mounted on a substrate. For example, the electronics assembly 120 can include one or more processors, capacitors, etc., interconnected by electrical traces, vias, or other electrical connectors. The electronics components can be configured to perform sensing and pacing of the target tissue.

The biostimulator components, e.g., the energy source container, the electronics compartment 118 containing the electronics assembly 120, and the header assembly 110, can be arranged on the longitudinal axis 108. Accordingly, each component can extend along the longitudinal axis 108 and have a respective axial location relative to another component along the longitudinal axis 108. For example, the energy source container can be offset from the electronics compartment 118 in a proximal direction 122 and the header assembly 110 can be offset from the electronics compartment 118 in a distal direction 124.

Referring to FIG. 2, a sectional view of a header assembly mounted on a housing of a leadless biostimulator is shown in accordance with an embodiment. The biostimulator 100 can be implanted in a body region having fluids, e.g., within the blood of a heart chamber, and thus, portions of the biostimulator 100 can be sealed and/or protected against fluid ingress that may compromise functionality of the biostimulator 100. For example, portions of the electrical feedthrough assembly 112, such as a flange 202, may be coated with a protective coating to prevent short circuiting of the distal electrode 104 and the proximal electrode 106.

Figure 6:
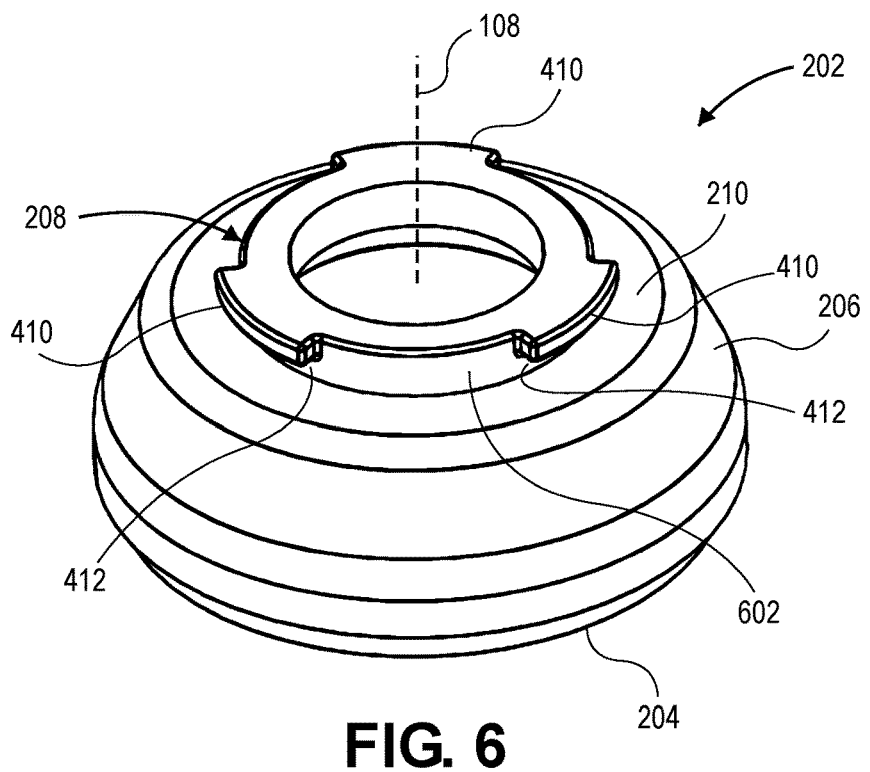
FIG. 6 is a top perspective view of a flange of a header assembly for a leadless biostimulator, in accordance with an embodiment.

In certain implementations, each of the components of the electrical feedthrough assembly 112 may be symmetrically formed about the longitudinal axis 108. For example, the cross-sectional area of the flange 202 illustrated in FIG. 2 can be swept about the longitudinal axis 108 such that the outer surface has a profile as shown in FIG. 6. In other implementations, the profiles of the components of the electrical feedthrough assembly 112 may be non-cylindrical. For example, a cross-section of the flange 202 taken about a transverse plane extending orthogonal to the longitudinal axis 108 may reveal an outer surface of the flange 202 that is square, pentagonal, elliptical, etc., or any other suitable shape. Accordingly, the particular shapes illustrated in the figures are provided by way of example only and not necessarily by way of limitation.

The electrical feedthrough assembly 112 of the header assembly 110 can include the flange 202. The flange 202 can be connected to the housing 102. For example, a proximal flange end 204, e.g., a lip, may be mounting on a distal end of the housing wall that surrounds the electronics compartment 118. In one implementation, the flange 202 is formed from titanium. The flange 202 can be mounted on the housing 102 and connected to the housing 102 by a hermetic seal, e.g., a weld or any other similar hermetically sealed connection. For example, the hermetic weld can be formed circumferentially around a seam between the proximal flange end 204 and the distal end of the housing wall.

In an embodiment, the flange 202 includes a shoulder 206. The flange 202 can have a flange 202 wall extending distally from the proximal flange end 204 to the shoulder 206, and the flange 202 can extend radially inward from the shoulder 206 toward a flange connector 208. The flange connector 208 can receive the helix mount 114, as described below. The shoulder 206 can be a transition region between the flange wall that extends substantially longitudinally from the proximal flange end 204 to the flange wall that extends substantially transversely. In an embodiment, the shoulder 206 has a distal shoulder surface 210. The distal shoulder surface 210 can be a surface of the flange 202 wall that extends substantially transversely, and thus, the distal shoulder surface 210 can extend transverse to the longitudinal axis 108. Accordingly, the distal shoulder surface 210 can face the distal direction.

In an embodiment, the flange 202 includes a flange channel 212 extending along the longitudinal axis 108 from the proximal flange end 204 to a distal flange end 214. The shoulder 206 of the flange 202 can extend around and circumferentially surround the flange channel 212. Similarly, the flange connector 208 can extend around and circumferentially surround the flange channel 212. Accordingly, the shoulder 206 and the flange connector 208 can define the flange channel 212 that contains a portion of the electronic assembly 120 and/or portions of the electrical feedthrough assembly 112, as described below.

The flange connector 208 can extend distally from the distal shoulder surface 210 along the longitudinal axis 108. For example, the flange connector 208 can extend in the distal direction from a proximal connector end 216 at the distal shoulder surface 210 to the distal flange end 214 at a distalmost location of the flange 202. The flange connector 208 can extend around and/or surround the longitudinal axis 108 between the shoulder 206 and the distal flange end 214. For example, one or more portions of the flange connector 208 can be annular wall portions that encircle the longitudinal axis 108. Accordingly, the flange connector 208 can include an outer surface facing radially outward from the longitudinal axis 108 and an interior surface facing radially inward toward the longitudinal axis 108. The interior surface can define a portion of the flange channel 212 extending through the flange connector 208 to provide a passage between a proximal side and a distal side of the electrical feedthrough assembly 112.

In one implementation, the header assembly 110, and more particularly the electrical feedthrough assembly 112, includes at least one of the electrodes. For example, the electrical feedthrough assembly 112 can include the distal electrode 104, which may be disposed within the flange channel 212. In an embodiment, the distal electrode 104 may include an electrode body 220 and/or an electrode tip 222. The electrode tip 222 may be mounted on the electrode body 220, e.g., on a distal end of the electrode body 220.

Feedthrough assemblies in accordance with the present disclosure may include a monolithic electrode body. For example, the monolithic electrode body can have several distinct portions that are integrally formed with each other. In one implementation, the electrode body 220 includes an electrode cup 224 and an electrode pin 226 that are integrally formed such that the electrode body 220 is monolithic, or, in other words, has a unitary or single-piece construction. More particularly, the electrode cup 224 and the electrode pin 226 can be formed from a single blank of material, such as 90/10 platinum/iridium alloy or another suitable conductive alloy, to produce the electrode body 220 such that the electrode body 220 does not have any seams, welds, etc. The electrode pin 226 can be sized to fit within a channel of the helix mount 114, as described below, and accordingly, the monolithic electrode body 220 provides an electrical pathway from the electronics compartment 118 (proximal to the helix mount 114) to the electrode tip 222 (distal to the flange 202 and the helix mount 114). More particularly, the electrode cup 224 and the electrode pin 226 can serve as the electrically active path from the electronics assembly 120 contained within the electronics compartment 118 to the patient-contacting pacing electrode tip 222.

The biostimulator 100, and more particularly the electrical feedthrough assembly 112, can include a filler 228, such as a monolithic controlled release device (MCRD). The filler 228 may include a therapeutic material, and can be loaded into an electrode cavity 230 within the electrode cup 224. When the biostimulator 100 is implanted at the target site, blood can flow into the electrode cavity 230 through a hole in the electrode tip 222 and cause the filler 228 to elute the therapeutic agent. Elution of the filler 228 can be controlled by its own geometry, as well as by a size of the electrode cavity 230 and the geometry of the electrode body 220. Accordingly, a specified dose of the therapeutic agent can flow, or weep, from the MCRD through the tip hole to the target tissue at an implantation site of the biostimulator 100 within a patient. In at least one implementation, the therapeutic agent can include a corticosteroid, such as dexamethasone sodium phosphate, dexamethasone acetate, etc. When the therapeutic agent is consistently released into the target tissue, the controlled dose can reduce inflammation associated with the device implantation. Furthermore, the electrode tip 222 can be conductive, and electrically in contact with the electrode body 220, such that pacing impulses transmitted through the electrode body 220 from the electronics assembly 120 can travel through the electrode tip 222 to the target tissue. Thus, the electrical feedthrough assembly 112 can be a multifunction component that not only serves as the electrical pass-through from a hermetic package to a surrounding environment, but also serves other functions, such as providing a housing 102 for and directing tissue interaction with the therapeutic agent. It will be appreciated that the electrical feedthrough assembly 112 can be a filtered or unfiltered assembly, as is known in the art. More particularly, the electrical feedthrough assembly 112 can incorporate an integral EMI filter capacitor (filtered feedthrough assembly) or not (unfiltered feedthrough assembly).

Other embodiments of the electrical feedthrough assembly 112, and in particular other embodiments of the distal electrode 104, have been described in U.S. patent application Ser. No. 16/662,282, filed on Oct. 24, 2019, titled "BIOSTIMULATOR FEEDTHROUGH HAVING INTEGRATED ELECTRODE," the contents of which are incorporated herein by reference in their entirety. In the interest of brevity, the details of such embodiments are not repeated in detail here.

The flange 202 may be a portion of the proximal electrode 106, and thus, the electrical feedthrough assembly 112 may also include the proximal electrode 106. The electrodes of the biostimulator 100 may be in close proximity, separated by an electrode gap 232 extending radially between the flange 202 and the electrode 104. If blood were allowed to fill the electrode gap 232 between the distal electrode 104 and the flange 202, the electrodes 104 could be electrically shorted and pacing impulses may not properly pace the cardiac tissue. Accordingly, a barrier can be included in the biostimulator 100 to prevent blood from filling the electrode gap 232 and/or to block an electrical path between the flange 202 and the electrode 104. In an embodiment, the barrier includes the helix mount 114.

The header assembly 110, and more particularly the electrical feedthrough assembly 112, includes the helix mount 114. The helix mount 114 may be formed from an insulating material, such as a ceramic material. For example, the helix mount 114 may include a mount body 233 extending along the longitudinal axis 108 between a proximal mount end 238 and a distal mount end 240. The mount body 233 may include a ceramic portion 234. The ceramic portion 234 can include a ceramic such as alumina, ruby, glass, or another ceramic insulating material. The ceramic portion 234 may encompass the entire helix mount 114 body shown in FIG. 2, e.g., the helix mount 114 may be entirely ceramic. Alternatively, the helix mount 114 may be only partly ceramic, e.g., a portion of the helix mount 114 may be formed from a ceramic material and a portion of the helix mount 114 may be formed from a non-ceramic material. By way of example, the ceramic portion 234 of the helix mount 114 may be represented by the cross-hatched sectional area in FIG. 2, and the sectional areas outside of the cross-hatching may be formed by non-ceramic materials. The non-ceramic materials may include polyetherehterketone (PEEK), by way of example. The non-ceramic materials may be overmolded on the ceramic portion 234 to form such a hybrid helix mount 114.

The helix mount 114 may include a mount bore 250 extending along the longitudinal axis 108 through a distal portion and a proximal portion of the mount body 233. For example, the mount bore 250 may extend from the proximal mount end 238 to the distal mount end 240. By way of reference, the distal portion of the helix mount 114 may be the portion of the helix mount 114 that is longitudinally distal of the distal flange end 214 when the helix mount 114 is connected to the flange 202. By contrast, the proximal portion of the helix mount 114 may be the portion of the helix mount 114 that is longitudinally proximal of the distal flange end 214 when the helix mount 114 is connected to the flange 202.

The mount bore 250 can include a counterbore 252 extending through the distal portion of the mount body 233, and a through-bore 253 extending from the counterbore 252 through the proximal portion of the mount body 233. More particularly, the counterbore 252 can extend from the distal mount end 240 to a proximal bore face 254, and the through-bore 253 can extend along the longitudinal axis 108 from the proximal bore face 254 to the proximal mount end 238.

In an embodiment, the helix mount 114 holds the electrode 104 within the flange channel 212 of the flange 202. More particularly, the distal electrode 104 may be disposed within the mount bore 250 radially inward from the flange 202. For example, the electrode cup 224 may be disposed within the counterbore 252 of the mount bore 250 such that a proximal surface of the electrode cup 224 is apposed to the proximal bore face 254 of the counterbore 252. Similarly, the electrode pin 226 may be disposed within the through-bore 253 of the mount bore 250 (and within the flange channel 212) to extend from the electrode cup 224 through the proximal portion of the helix mount 114 and into the flange cavity to connect to the electronics assembly 120.

In an embodiment, the helix mount 114 isolates the flange 202 from the electrode 104. The helix mount 114 can both physically and electrically isolate the flange 202 from the electrode 104. The helix mount 114 can physically isolate the flange 202 from the electrode 104 by filling a space between those components. More particularly, there may be no gap between the flange 202 and the electrode 104 because the helix mount 114, whether formed from a ceramic or a non-ceramic material, may completely separate the flange 202 from the electrode 104 such that there is no space for blood to enter between the flange 202 and the electrode 104. Similarly, the ceramic portion 234 can be between the flange 202 and the electrode 104, and thus, may eliminate any electrical pathway between the components. As a result, the need for an additional gasket to fill a physical space or an additional insulator to block an electrical pathway is eliminated. Thus, it will be appreciated that the helix mount 114, which is integrated within the electrical feedthrough assembly 112 to physically separate and electrically isolate the flange 202 and the electrode 104, can reduce the number of components in the electrical feedthrough assembly 112 as compared to existing leadless pacemakers.

In an embodiment, the ceramic portion 234 is disposed between the flange 202 and the electrode 104. At least a portion of the cross-hatched sectional area shown, which represents the ceramic portion 234, may be radially between the flange 202 and the electrode 104. For example, a radial line extending outward from the longitudinal axis 108 from the electrode cup 224 or the electrode pin 226 may pass through the flange 202. The radial line, however, may also intersect the ceramic portion 234. Thus, the ceramic portion 234 can block a radially outward electrical path extending between the electrode 104 and the flange 202. More particularly, the ceramic portion 234 of the helix mount 114 can electrically isolate the distal electrode 104 from the flange 202.

The radial path between the flange 202 and the electrode 104 may or may not be a shortest path 256 between the flange 202 and the electrode 104. The shortest path 256 can be the path along a minimum distance between a surface of the flange 202 and a surface of the distal electrode 104. The shortest path 256 is represented in FIG. 2 by a dotted line that does not extend orthogonally to the longitudinal axis 108. The non-radial line is, of course, illustrated by way of example given that the shortest path 256 may actually extend radially from the flange connector 208 to a bottom portion of the electrode cup 224. In any case, the ceramic portion 234 of the helix mount 114 may be disposed between the flange 202 and the electrode 104 along the shortest path 256. For example, the shortest path 256 may intersect the ceramic portion 234. Thus, the shortest path 256, which represents a preferred electrical pathway between the flange 202 and electrode 104, may be blocked by the ceramic portion 234 of the helix mount 114.

In an embodiment, the helix mount 114 can include an annular section 236 (the region of the cross-hatched portion bounded by vertical dashed lines in FIG. 2) that completely separates and isolates the flange 202 from the electrode 104 within the electrical feedthrough assembly 112. The annular section 236 may extend from the proximal mount end 238 of the helix mount 114 to the distal mount end 240 of the helix mount 114. Accordingly, the electrode gap 232 between the flange 202 and the electrode 104 may be entirely filled by the annular section 236.

The annular section 236 may be partly or entirely ceramic. For example, the ceramic portion 234 of the helix mount 114 can include the annular section 236 such that an annular ceramic ring extends around the mount bore 250. When the annular section 236 extends longitudinally from the proximal mount end 238 to the distal mount end 240, the ceramic portion 234 circumferentially surrounds the mount bore 250, and the distal electrode 104 within the mount bore 250, from the proximal mount end 238 to the distal mount end 240. Alternatively, only a portion of the annular section 236 may be ceramic. Accordingly, the annular ceramic ring may extend longitudinally over only a portion of the distance between the proximal mount end 238 and the distal mount end 240. In either case, the ceramic portion 234 may be positioned to block any or all electrical pathways between the flange 202 and the electrode 104 through the helix mount 114.

Similar to the flange 202, the helix mount 114 may include a mount connector 260. Both the flange connector 208 and the mount connector 260 may be threadless connectors, as described below, used to couple the flange 202 to the helix mount 114. More particularly, the flange connector 208 may be coupled to the mount connector 260 to mechanically interlock the flange 202 and helix mount 114 components of the electrical feedthrough assembly 112.

In addition to the mechanical interlock provided by the flange connector 208 and the mount connector 260, the components of the electrical feedthrough assembly 112 may be secured by a joint 262. More particularly, a joint 262 may be formed between the flange 202, the helix mount 114, and the electrode 104, to hermetically seal the components and mechanically interlock the components. The joint 262 may be a thermal or adhesive weld. Alternatively, the joint 262 can include a filler metal. For example, the joint 262 may be a brazing joint 262 having a metal such as gold filling the spaces radially between the flange 202, the proximal portion of the helix mount 114, and the electrode pin 226. The entire proximal portion of the helix mount 114 may be ceramic to facilitate the brazing process, e.g., to withstand the high temperatures experienced during brazing. The joint 262 can completely fill any space between the electrical feedthrough assembly components to form a hermetic seal between the flange cavity and the environment distal to the flange 202.

It will be appreciated that the brazing process, when applied to the components of the electrical feedthrough assembly 112, introduces heat that can result in expansion of the component materials. Such expansion may be detrimental to threaded connectors having tight thread tolerances. For example, existing leadless pacemakers that incorporate threaded connections between the helix mount 114 and the flange 202 may experience mechanical failures from the high brazing temperatures. The threadless connectors of the electrical feedthrough assembly 112 described herein, however, may have looser tolerances that allow the connectors to function regardless of whether the connectors expand during the brazing process.

In an embodiment, the helix mount 114 includes a mount flange 270. The fixation element 116 can be mounted on the mount flange 270. In one implementation, the fixation element 116 includes a helix 280. The helix 280 can be screwed onto the mount flange 270 around the mount body 233. The helix 280 can extend distally from the helix mount 114 about the longitudinal axis 108. For example, the helix 280 can revolve about the longitudinal axis 108. The helix 280 can include a spiral wire, formed by coiling or cut from a wall of a length of tubing, which extends in a rotational direction around the longitudinal axis 108. For example, the helix 280 can revolve in a right-handed direction about the longitudinal axis 108. The helix 280 can be suitable for attaching the biostimulator 100 to tissue, such as heart tissue. For example, in the case of a right-handed spiral direction, the biostimulator 100 can be advanced into contact with a target tissue, and the biostimulator 100 can then be rotated in the right-handed direction to screw the helix 280 into the tissue. Torque can be transmitted from the housing 102 to the helix 280 through the electrical feedthrough assembly 112 and helix mount 114.

Figure 3:
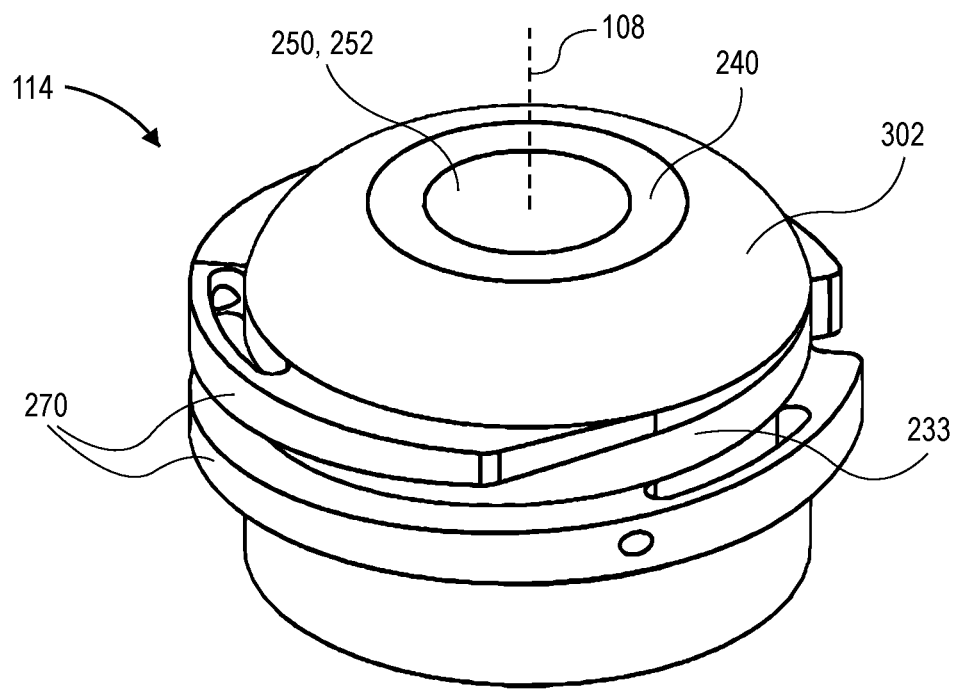
FIG. 3 is a top perspective view of a helix mount of a header assembly for a leadless biostimulator, in accordance with an embodiment.

Referring to FIG. 3, a top perspective view of a helix mount of a header assembly for a leadless biostimulator is shown in accordance with an embodiment. The mount flange 270 can extend helically about the longitudinal axis 108. The mount flange 270 can extend radially outward from the mount body 233, providing a helical ledge onto which the fixation element 116 may be placed. The mount body 233 may have a cylindrical outer surface that extends along the longitudinal axis 108 and transitions into an atraumatic end 302. For example, the atraumatic end 302 can have a curved surface, e.g., a bulbous surface, that transitions from the cylindrical surface inward toward the distal mount end 240. As described above, the counterbore 252 of the mount bore 250 can extend proximally from the distal mount end 240 into the mount body 233 along the longitudinal axis 108.

Figure 4:
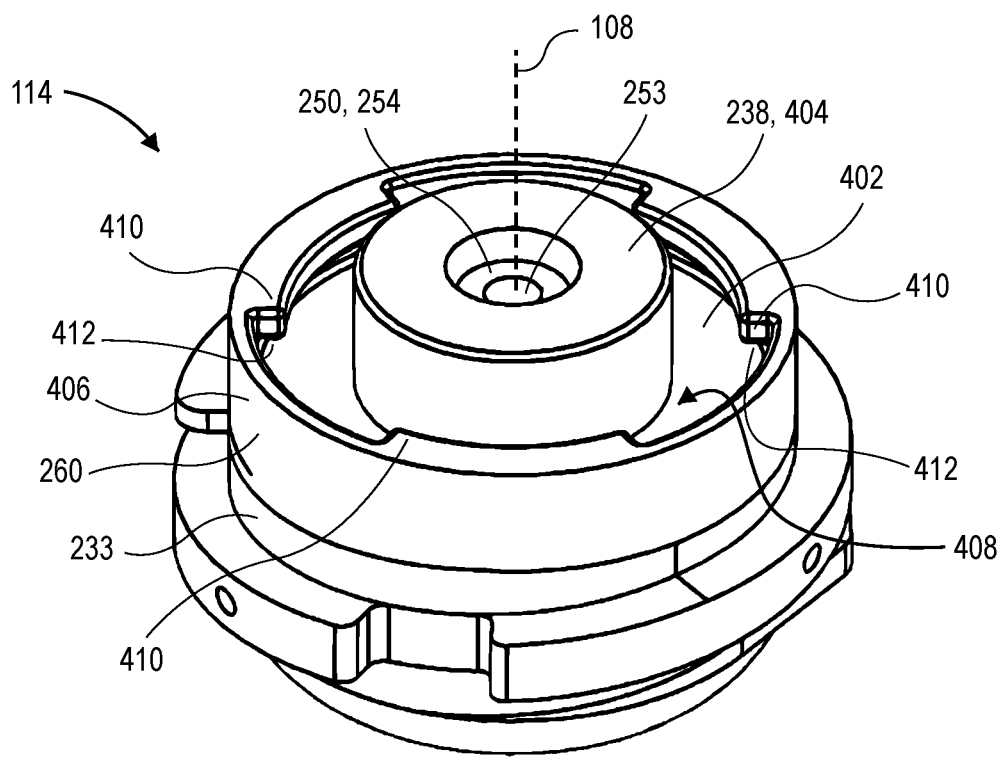
FIG. 4 is a bottom perspective view of a helix mount of a header assembly for a leadless biostimulator, in accordance with an embodiment.

Referring to FIG. 4, a bottom perspective view of a helix mount of a header assembly for a leadless biostimulator is shown in accordance with an embodiment. The mount connector 260 of the helix mount 114 can extend proximally from the distal portion of the mount body 233. More particularly, a longitudinal boundary between the distal portion and the proximal portion of the mount body 233 may be provided by a proximal mount face 402, and the mount connector 260 can extend proximally from the proximal mount face 402. As described below, the proximal mount face 402 may appose the distal flange end 214 when the helix mount 114 is mounted on the flange 202.

The proximal portion of the mount body 233 may include a mount boss 404. The mount boss 404 can protrude proximally along the longitudinal axis 108 from the proximal mount face 402 to the proximal mount end 238. The mount boss 404 may extend into and fill the flange channel 212 radially inward from the flange connector 208 (FIG. 2).

Accordingly, the through-bore 253 of the mount bore 250 may extend along the longitudinal axis 108 through the mount boss 404.

In an embodiment, the mount connector 260 extends around the proximal portion of the mount body 233. For example, the mount connector 260 can include a mount rim 406 that extends longitudinally from the proximal mount face 402 and circumferentially around the mount boss 404. The mount rim 406 can be an annular wall radially offset from the mount boss 404 such that an annular receiving channel 408 is defined radially between the mount connector 260, e.g., the mount rim 406, and the proximal portion of the mount body 233, e.g., the mount boss 404.

In addition to the mount rim 406, the mount connector 260 may include several mating prongs 410 extending radially from the mount rim 406. The mating prongs 410 are shown extending radially inward from the mount rim 406, however, it will be appreciated that the mount connector 260 may be located radially inward from the flange connector 208, and thus, the mating prongs 410 may instead extend radially outward from the mount rim 406. Accordingly, the radial location of the mount connector 260 relative to the flange connector 208 is intended to be illustrative and not limiting.

The overhang of the mating prongs 410 can define several mating channels 412 configured to receive corresponding mating prongs 410 of the flange connector 208. More particularly, the annular receiving channel 408 can include the several mating channels 412 defined between the mating prongs 410 and the distal portion of the mount body 233, e.g., the proximal mount face 402.

Figure 5:
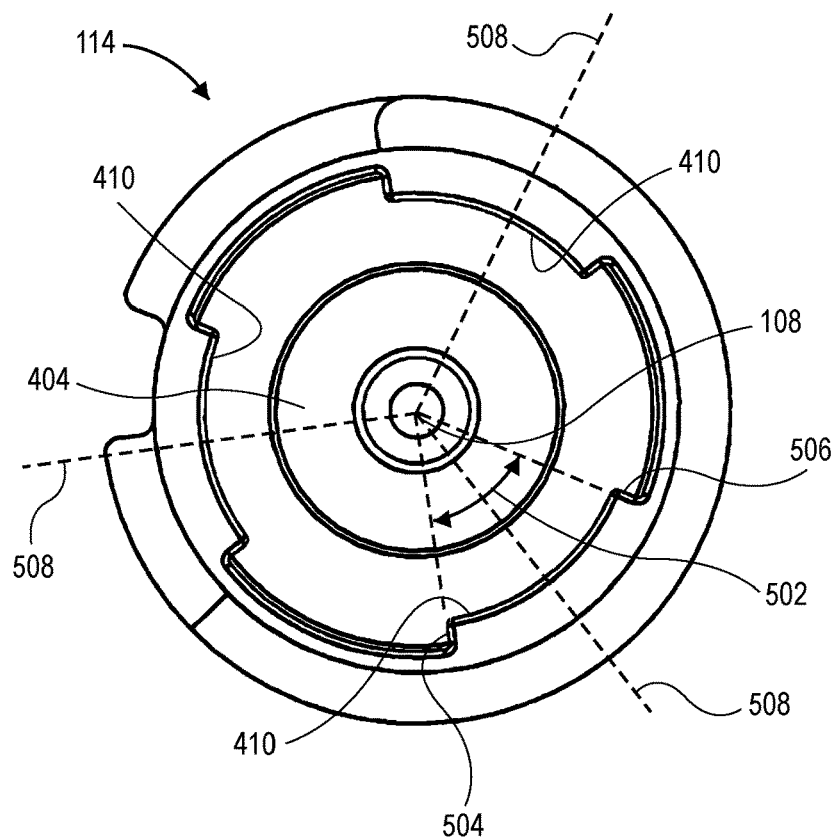
FIG. 5 is a bottom view of a helix mount of a header assembly for a leadless biostimulator, in accordance with an embodiment.

Referring to FIG. 5, a bottom view of a helix mount of a header assembly for a leadless biostimulator is shown in accordance with an embodiment. The bottom view illustrates a distribution of the mating prongs 410 about the longitudinal axis 108. In an embodiment, each mating prong 410 has a prong width 502 extending through an angle having a vertex at the longitudinal axis 108. The angle can traverse from a first prong end 504 to a second prong end 506. A midline 508 can extend from the longitudinal axis 108 through the mating prong 410 at a location equidistant from the prong ends. An annular separation between the respective midlines of the mating prongs 410 can define a distribution of the mating prongs 410 about the longitudinal axis 108. In an embodiment, the mating prongs 410 of the mount connector 260 are evenly distributed about the longitudinal axis 108. For example, when the mount connector 260 includes three mating prongs 410 as shown, the respective midlines of the mating prongs 410 may be separated from each other by an angle of 120 degrees. Similarly, when the mount connector 260 includes four mating prongs 410, the respective midlines of the mating prongs 410 may be separated from each other by 90 degrees. In other embodiments, the mating prongs 410 may not be evenly distributed, e.g., a separation between midlines of a first pair of mating connectors may be different than a separation between midlines of the second pair of mating connectors.

Any or all of the portions of the helix mount 114 described above, e.g., the mount body 233, the mount flange 270, or the mount connector 260, may be formed partly or entirely from ceramic. For example, the mount body 233, the mount flange 270, and the mount connector 260 may be entirely ceramic. Accordingly, the helix mount 114 may be formed using known ceramic manufacturing processes, e.g., ceramic sintering, to form a monolithic helix mount 114 having the features described above.

Referring to FIG. 6, a top perspective view of a flange of a header assembly for a leadless biostimulator is shown in accordance with an embodiment. The top perspective view shows the outer surface of the flange 202, e.g., the shoulder 206 and the distal shoulder surface 210 revolved about the longitudinal axis 108. A proximal portion of the flange 202 can form a circumferential shell around the longitudinal axis 108, which when mounted on the housing 102, encloses the flange cavity.

The flange 202, like the helix mount 114, can include a threadless connector, e.g., the flange connector 208. In an embodiment, the flange connector 208 extends circumferentially around the longitudinal axis 108. For example, the flange connector 208 can include a flange rim 602 that extends longitudinally from the distal shoulder surface 210 and circumferentially around the longitudinal axis 108. The flange rim 602 can be an annular wall having a cylindrical outer surface.

In addition to the flange rim 602, the flange connector 208 may include several mating prongs 410 extending radially from the flange rim 602. The mating prongs 410 are shown extending radially outward from the flange rim 602, however, it will be appreciated that the flange connector 208 may be located radially outward from the mount connector 260, and thus, the mating prongs 410 may instead extend radially inward from the flange rim 602. Accordingly, the radial location of the flange connector 208 relative to the mount connector 260 is intended to be illustrative and not limiting.

The overhang of the mating prongs 410 can define several mating channels 412 configured to receive corresponding mating prongs 410 of the mount connector 260. More particularly, the mating channels 412 can be defined between the mating prongs 410 and the distal shoulder surface 210.

Figure 7:
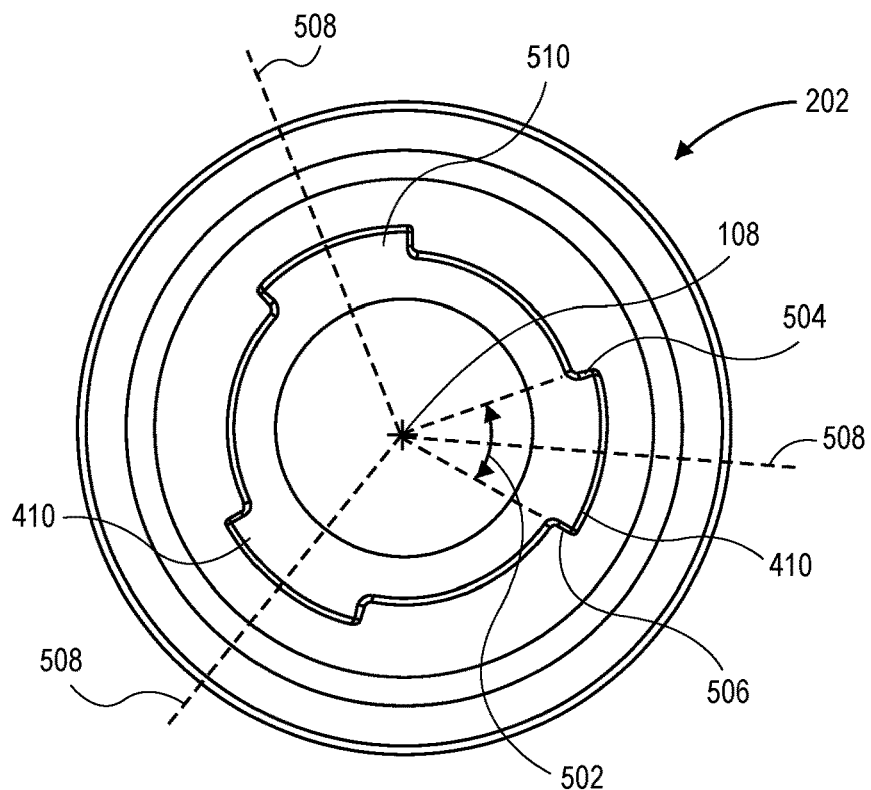
FIG. 7 is a top view of a flange of a header assembly for a leadless biostimulator, in accordance with an embodiment.

Referring to FIG. 7, a top view of a flange of a header assembly for a leadless biostimulator is shown in accordance with an embodiment. The top view illustrates a distribution of the mating prongs 410 about the longitudinal axis 108. In an embodiment, each mating prong 410 has a prong width 502 extending through an angle having a vertex at the longitudinal axis 108. The angle can traverse from a first prong end 504 to a second prong end 506. A midline 508 can extend from the longitudinal axis 108 through the mating prong 410 at a location equidistant from the prong ends. An annular separation between the respective midlines of the mating prongs 410 can define a distribution of the mating prongs 410 about the longitudinal axis 108. In an embodiment, the mating prongs 410 of the flange connector 208 are evenly distributed about the longitudinal axis 108. For example, when the flange connector 208 includes three mating prongs 410 as shown, the respective midlines of the mating prongs 410 may be separated from each other by an angle of 120 degrees. Similarly, when the flange connector 208 includes four mating prongs 410, the respective midlines of the mating prongs 410 may be separated from each other by 90 degrees. In other embodiments, the mating prongs 410 may not be evenly distributed, e.g., a separation between midlines of a first pair of mating connectors may be different than a separation between midlines of the second pair of mating connectors.

Figure 8:
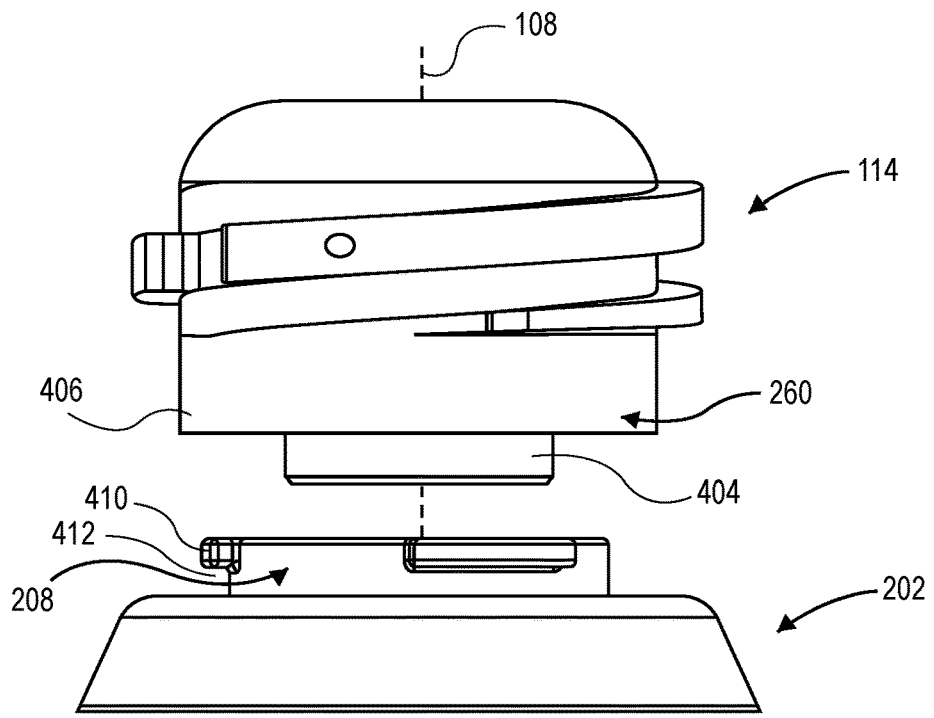
FIG. 8 is a side view of a helix mount being mounted on a flange, in accordance with an embodiment.

Referring to FIG. 8, a side view of a helix mount being mounted on a flange is shown in accordance with an embodiment. As described above, the flange connector 208, like the mount connector 260, can include several mating prongs 410 and several mating channels 412 distributed about the longitudinal axis 108. In an embodiment, the flange connector 208 is a male coupling and the mount connector 260 is a female coupling. More particularly, the flange connector 208 can be received by the mount connector 260. When the flange connector 208 and the mount connector 260 are assembled, the mount boss 404 can insert into the flange channel 212 of the flange 202. Similarly, the flange connector 208 can insert into the annular channel of the helix mount 114. Accordingly, the flange connector 208 can be radially between the mount boss 404 and the mount rim 406, as shown in FIG. 2.

Figure 9A:
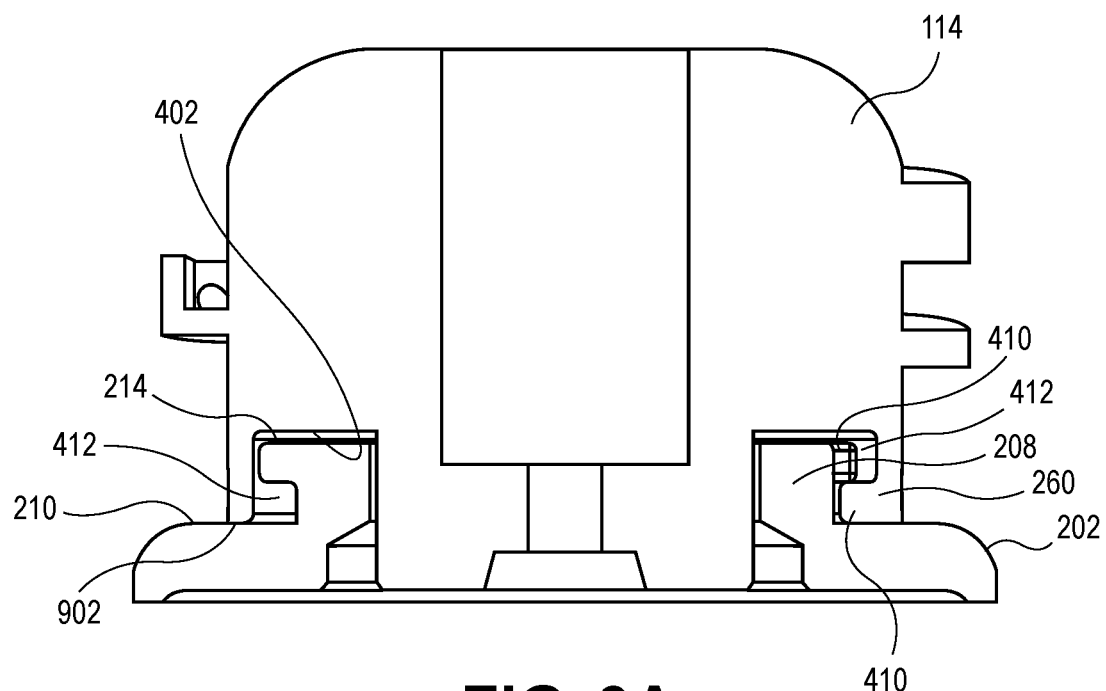
FIGS. 9A-9B are sectional views of a helix mount being twisted from an unlocked state to a locked state on a flange, in accordance with an embodiment.
Figure 10A:
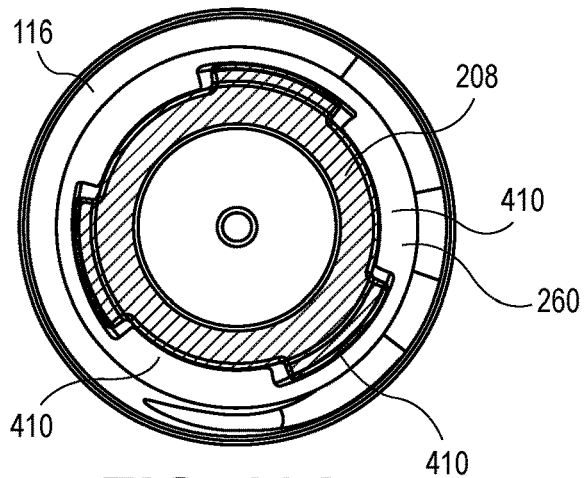
FIGS. 10A-10C are sectional views of a helix mount being twisted from an unlocked state to a locked state on a flange, in accordance with an embodiment.

Referring to FIG. 9A, a sectional view of a helix mount in an unlocked state is shown in accordance with an embodiment. Upon initial insertion of the flange connector 208 into the mount connector 260, the connectors can be in an unlocked state. In the unlocked state, the mating prongs 410 are not overlapping in the longitudinal direction (FIG. 10A). More particularly, the mating prongs 410 of the flange 202 may be lined up with slots circumferentially between the mating prongs 410 of the helix mount 114. Although the mating channels 412 may be configured to receive the mating prongs 410, in the unlocked state the mating prongs 410 may be located outside of the mating channels 412. Accordingly, the components can be easily separated in the unlocked state.

Figure 9B:
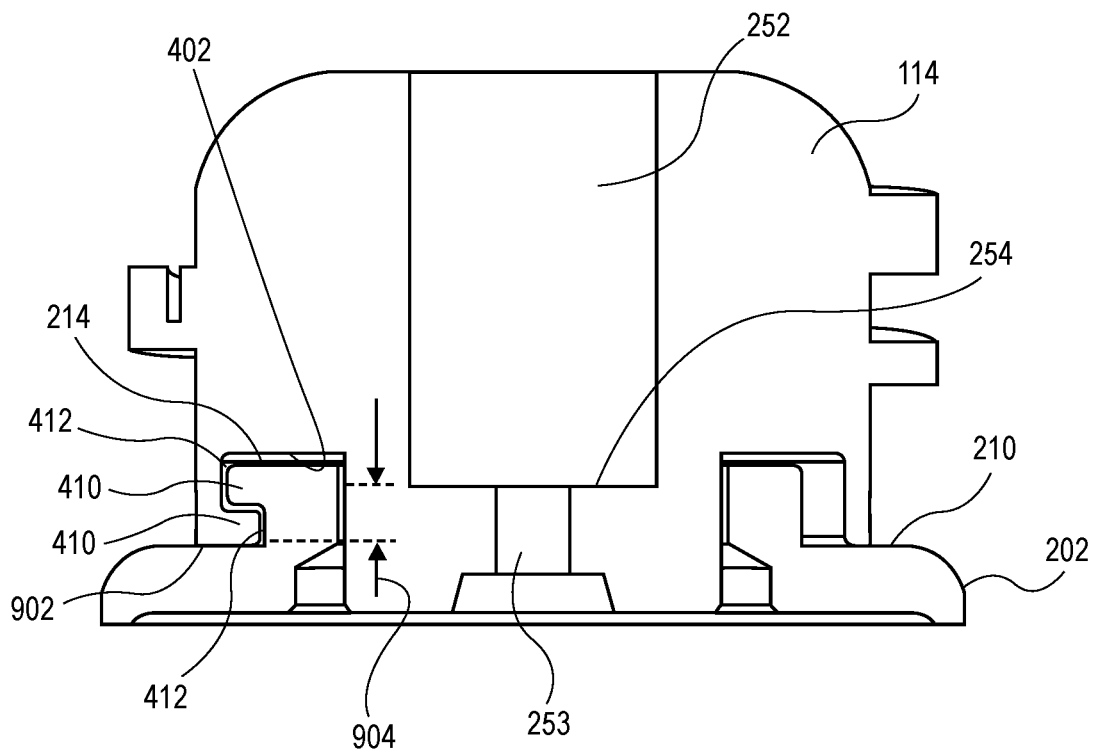

Referring to FIG. 9B, a sectional view of a helix mount in a locked state is shown in accordance with an embodiment. After lowering the helix mount 114 onto the flange 202 to place the components in the unlocked state, the helix mount 114 may be twisted relative to the flange 202 to move the components into a locked state. In the locked state, the mating prongs 410 of the flange 202 can overlap the mating prongs 410 of the helix mount 114 in the longitudinal direction. More particularly, the mating prongs 410 of the flange connector 208 can rotate into the mating channels 412 of the mount connector 260, and the mating prongs 410 of the flange connector 208 can rotate into the mating channels 412 of the flange connector 208. The mounting prongs can therefore interfere and resist axial movement between the helix mount 114 and the flange 202. Such resistance can reduce the likelihood that the helix mount 114 will dislodge from the flange 202 during use and/or retrieval of the biostimulator 100 from the patient.

The interface between the helix mount 114 and the flange 202 provided by the mount connector 260 and the flange connector 208 can provide self-alignment of the distal electrode 104 to a particular height. When the helix mount 114 is inserted onto the flange 202, as shown in FIGS. 9A-9B, a contact 902 may be formed between the helix mount 114 and the flange 202. The contact 902 may be between the distal shoulder surface 210 and a proximal end of the mount connector 260, in an embodiment. In other embodiments, the contact 902 may be located elsewhere. For example, the contact 902 may optionally be between the distal flange end 214 and the proximal mount face 402 (not shown).

The contact 902 between the flange 202 and the helix mount 114 provides a datum relative to which the proximal bore face 254 of the counterbore 252 may be located to ensure that the electrode cup 224 is consistently positioned. More particularly, the proximal bore face 254 can be longitudinally offset from the contact 902 by a predetermined distance 904. Advantageously, as compared to existing pacemakers that require tightly controlled manufacturing processes to ensure that the electrode 104 and the additional insulator component are properly located relative to the flange 202, the integrated helix mount 114 provides for self-alignment. More particularly, given that the contact 902 on the helix mount 114 is spaced apart from the proximal bore face 254 of the counterbore 252 by the predetermined distance 904 (and the predetermined distance 904 is built into the manufacture of the helix mount 114 component) the helix mount 114 may simply be twisted onto the flange connector 208 without specialized height alignment operations to produce the desired offset between the proximal bore face 254 and the flange 202. By extension, when the distal electrode 104 is mounted within the counterbore 252, a desired offset and critical height alignment between the distal electrode 104 and the flange 202 can be easily achieved. Accordingly, the integrated helix mount 114 can reduce manufacturing burdens associated with the alignment of component heights.

Referring to FIG. 10A, a sectional view of a helix mount in an unlocked state is shown in accordance with an embodiment. In the unlocked state, the mounting prongs of the flange connector 208 are disposed within the slots located circumferentially between the mounting prongs of the mount connector 260. The unlocked state shown in FIG. 10A corresponds to the unlocked state shown in FIG. 9A. Accordingly, the helix mount 114 can be easily removed from the flange 202 in the longitudinal direction when the assembly is unlocked.

Figure 10B:
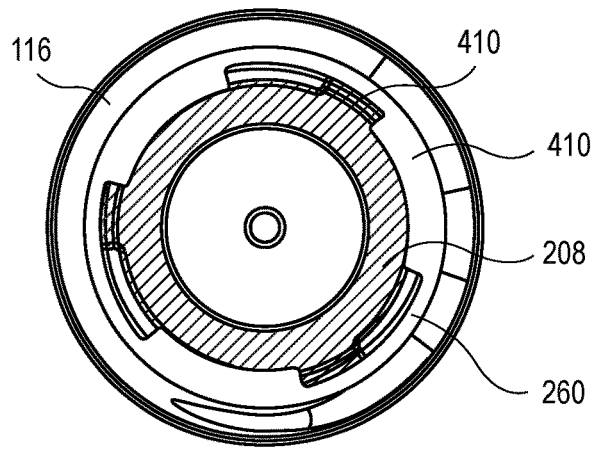

Referring to FIG. 10B, a sectional view of a helix mount in an intermediate state is shown in accordance with an embodiment. In the intermediate state, the mounting prongs of the flange connector 208 and the mount connector 260 partially overlap in the longitudinal direction. More particularly, as the helix mount 114 is twisted on the flange 202, the mounting prongs of the flange connector 208 are partially received within the mounting channels of the mount connector 260 (hidden behind the mounting tabs of the mount connector 260). The partial overlap between the mounting prongs creates an interference that resists longitudinal movement between the helix mount 114 and the flange 202. Accordingly, the intermediate state may be a partially locked state.

Figure 10C:
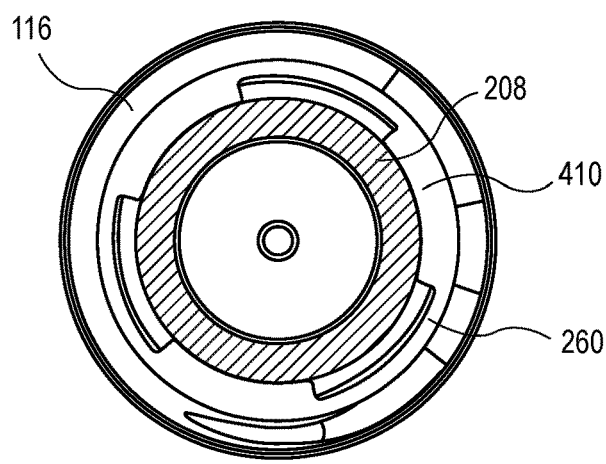

Referring to FIG. 10C, a sectional view of a helix mount in a locked state is shown in accordance with an embodiment. In the locked state, the mounting prongs of the flange connector 208 and the mount connector 260 fully overlap in the longitudinal direction. More particularly, the helix mount 114 is twisted to the locked state, in which the mounting prongs of the flange connector 208 are fully received within the mounting channels of the mount connector 260 (hidden behind the mounting tabs of the mount connector 260). The overlap between the mounting prongs creates an interference that resists longitudinal movement. The locked state shown in FIG. 10C corresponds to the locked state shown in FIG. 9B. Accordingly, the helix mount 114 can be mechanically secured to the flange 202 such that a likelihood of removal of the helix mount 114 from the flange 202 is reduced.

Figure 11:
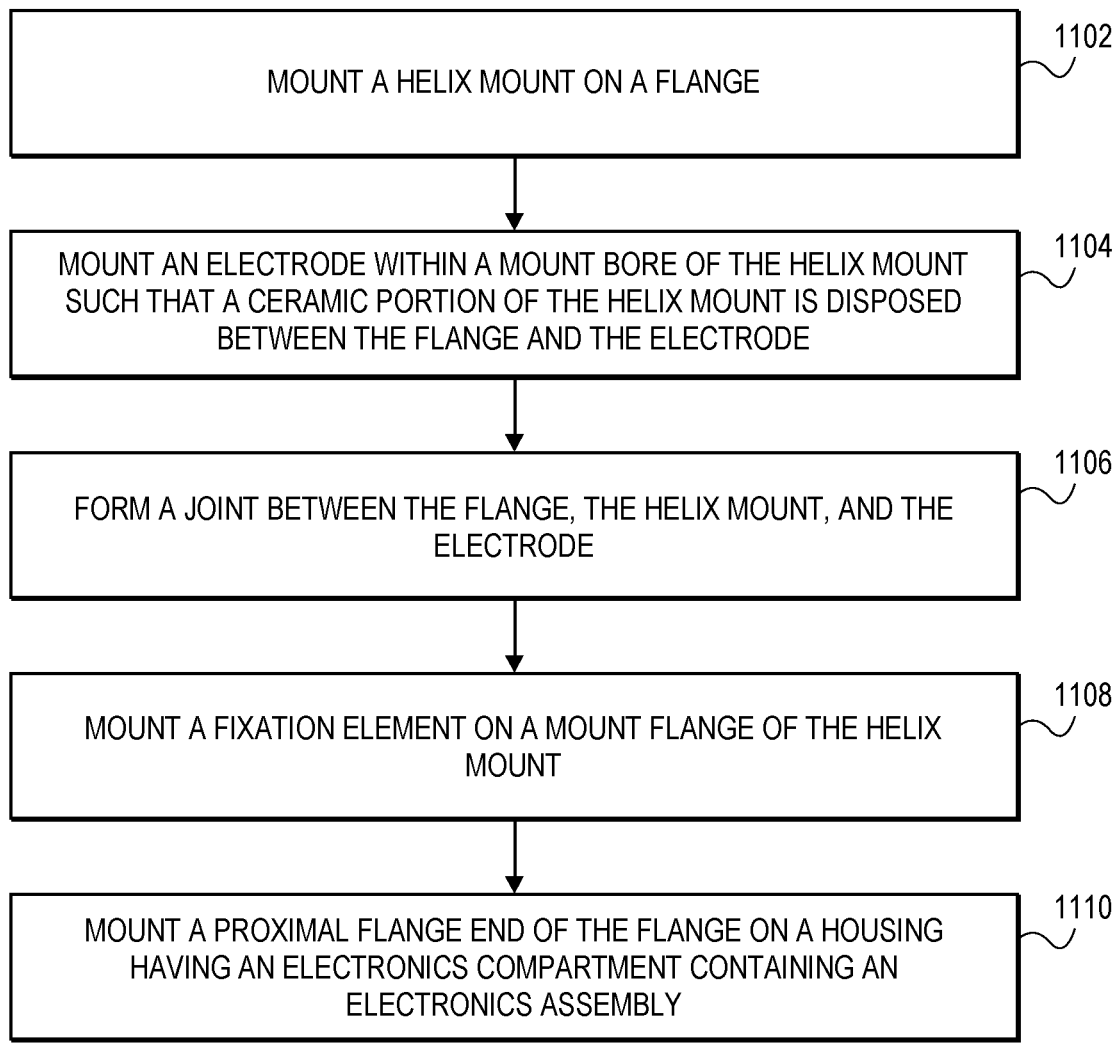
FIG. 11 is a flowchart of a method of manufacturing a header assembly for a leadless biostimulator, in accordance with an embodiment.

Referring to FIG. 11, a flowchart of a method of manufacturing a header assembly for a leadless biostimulator is shown in accordance with an embodiment. It will be appreciated that, based on the above description, the process of manufacturing electrical feedthrough assembly 112 may be simplified compared to the processes used to assemble existing leadless pacemakers. More particularly, integration of the helix mount 114 into the electrical feedthrough assembly 112 eliminates the need for additional components, such as an additional insulator or a gasket, and thus, fewer process operations may be required to assemble the electrical feedthrough assembly 112. The method of manufacturing the header assembly 110 having the helix mount 114 incorporated in the electrical feedthrough assembly 112 can therefore represent a markedly more efficient manufacturing method for a leadless biostimulator 100.

At operation 1102, the helix mount 114 is mounted on the flange 202. The mounting operation was described above with respect to FIGS. 9A-10C. The helix mount 114 can be lowered onto the flange 202 until the contact 902 is formed between the helix mount 114 and the flange 202. The helix mount 114 can then be twisted to cause the flange connector 208 to engage the mount connector 260, and to move the components from the unlocked state to the locked state.

In an embodiment, when the flange connector 208 and the mount connector 260 are engaged in the locked state, the components may resist movement toward the unlocked state. The resistance to movement may be achieved in numerous manners. For example, the mounting prongs may have surfaces that taper in a circumferential direction such that, as the mounting prongs are received within the mounting channels, apposing surfaces of the mounting prongs slide over each other and press against each other to form a press fit. The press fit can resist back out of the mounting prongs to retain the helix mount 114 in the locked state. Alternatively, the flange connector 208 and the mount connector 260 may be bonded to each other after the components are placed in the locked state. For example, a medical adhesive may be flowed into the gap between the mounting prongs of the flange connector 208 and the mount connector 260 to bond and retain the connectors in the locked state. Similarly, a joint 262 may be formed between the connectors, e.g. by brazing, such that a filler metal or a weld secures the connectors and retains the connectors in the locked state.

At operation 1104, the electrode 104 is mounted within the mount bore 250 of the helix mount 114. When the electrode 104 is placed within the mount bore 250, the ceramic portion 234 of the helix mount 114 can be disposed between the flange 202 and the electrode 104. Accordingly, the helix mount 114 incorporated in the electrical feedthrough assembly 112 physically separates and electrically isolates the flange 202 from the electrode 104.

Based on the predetermined distance 904 between the proximal bore face 254 and the contact 902, insertion of the electrode cup 224 into the counterbore 252 ensures that a proximal end of the electrode cup 224 is properly located relative to the flange 202. Similarly, the repeatable positioning of the electrode cup 224 within the counterbore 252 ensures that the electrode pin 226 extends to a predetermined distance 904 into the flange cavity. Such repeatable positioning can ensure that the electrode pin 226 is properly located relative to the electrical connectors on the electronics assembly 120. Accordingly, when the electrode 104 is mounted into the helix mount-flange subassembly in the locked state, an accurately positioned electrical feedthrough assembly 112 is formed.

At operation 1106, the joint 262 is formed between the flange 202, the helix mount 114, and the distal electrode 104. The components can be brazed as a single subassembly, and thus, the joint 262 may be a brazing joint 262. In such case, the joint 262 includes the filler metal, as described above. The filler metal can join the feedthrough components and seal spaces between the components such that the electrical feedthrough assembly 112 provides a mechanically secure and hermetic seal to separate the flange cavity from the environment distal to the flange 202.

At operation 1108, the fixation element 116 is mounted on the mount flange 270 of the helix mount 114. The helix 280 of the fixation element 116 can be screwed into the helical holding thread provided by the mount flange 270. The fixation element 116 can hold the electrical feedthrough assembly 112 in close contact to the target tissue via the helix mount 114 during clinical use.

In other example operations, the filler 228 can be inserted in the electrode cavity 230 and/or the electrode tip 222 can be mounted on a distal end of the electrode cup 224. For example, the electrode tip 222 can be placed in contact with the distal end around a circumference of the distal end. The electrode tip 222 can then be joined to the electrode body 220 by a circumferential bond. For example, an adhesive or thermal weld may be formed between the distal end of the electrode cup 224 and the electrode tip 222.

At operation 1110, the assembled header assembly 110 may be mounted on the housing 102 of the biostimulator 100. More particularly, the proximal flange end 204 of the flange 202 can be mounted on the distal end of the housing wall. The electrical feedthrough assembly 112 can be permanently bonded to the housing 102 by a weld, or an alternative type of bond. In the assembled state, the electrical feedthrough assembly 112 can connect to the electronics assembly 120 within the electronics compartment 118 to transmit sensing and/or pacing pulses from the electronics compartment 118 to the target tissue.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A header assembly for a leadless biostimulator, comprising:
   a flange including a distal flange end and a flange channel extending along a longitudinal axis;
   an electrode disposed within the flange channel; and
   a helix mount having a plurality of ceramic portions including a mount body, a mount flange, a mount connector, and a mount boss, wherein the mount body has a proximal mount face apposed to the distal flange end, the mount flange extends radially outward from the mount body and helically about the longitudinal axis, and wherein the mount connector and the mount boss protrude proximally from the proximal mount face to form an annular channel receiving the flange such that the mount boss is between the flange and the electrode.

2. The header assembly of claim 1, wherein the mount boss is radially between the flange and the electrode.

3. The header assembly of claim 1, wherein a shortest path between the flange and the electrode intersects the mount boss of the helix mount.

4. The header assembly of claim 1, wherein the mount boss includes an annular section of the helix mount extending from a proximal mount end of the helix mount to a distal mount end of the helix mount.

5. The header assembly of claim 4, wherein the helix mount includes a mount bore extending along the longitudinal axis from the proximal mount end to the distal mount end, wherein the annular section extends around the mount bore, and wherein the electrode is disposed within the mount bore.

6. The header assembly of claim 5, wherein the mount bore includes a counterbore having a proximal bore face, and wherein the proximal bore face is longitudinally offset by a predetermined distance from a contact point between the flange and the helix mount.

7. The header assembly of claim 1, wherein a flange connector of the flange is coupled to the mount connector of the helix mount, and wherein the flange connector and the mount connector are threadless connectors.

8. The header assembly of claim 7, wherein the flange connector and the mount connector include a plurality of mating channels and a plurality of mating prongs, wherein the plurality of mating channels are configured to receive the plurality of mating prongs.

9. The header assembly of claim 1 further comprising a joint between the flange, the helix mount, and the electrode, wherein the joint includes a filler metal.

10. The header assembly of claim 1 further comprising a fixation element mounted on the mount flange of the helix mount, wherein the fixation element includes a helix revolving about the longitudinal axis.

11. The header assembly of claim 1 further comprising a housing having an electronics compartment containing an electronics assembly, wherein a proximal flange end of the flange is mounted on the housing.

12. The header assembly of claim 1, wherein the helix mount is entirely ceramic.

13. A helix mount for a leadless biostimulator, comprising:
    a mount body extending along a longitudinal axis between a proximal mount end and a distal mount end, wherein a mount bore extends along the longitudinal axis through the mount body, and wherein the mount body includes a proximal mount face;
    a mount flange extending radially outward from the mount body, wherein the mount flange extends helically around the longitudinal axis;
    a mount connector; and
    a mount boss, wherein the mount boss and the mount connector protrude proximally from the proximal mount face to form an annular channel between the mount connector and the mount boss, and wherein the mount boss is ceramic.

14. The helix mount of claim 13, wherein the mount boss includes an annular section extending around the mount bore from the proximal mount end to the distal mount end.

15. The helix mount of claim 13, wherein the mount bore includes a counterbore extending through a distal portion of the mount body along the longitudinal axis from the distal mount end to a proximal bore face, and a through-bore extending through a proximal portion of the mount body along the longitudinal axis from the proximal bore face to the proximal mount end.

16. The helix mount of claim 15, wherein the mount connector includes a plurality of mating prongs extending radially from a mount rim, and wherein the annular channel includes a plurality of mating channels defined between the plurality of mating prongs and the distal portion of the mount body.

17. The helix mount of claim 15, wherein the mount body, the mount flange, and the mount connector are entirely ceramic.

18. A header assembly for a leadless biostimulator, comprising:
    a flange include a shoulder and a flange connector, wherein the shoulder has a distal shoulder surface, wherein the shoulder extends around a flange channel disposed on a longitudinal axis, wherein the flange connector extends distally from the distal shoulder surface to a distal flange end along the longitudinal axis and around the flange channel, and wherein the flange connector is a threadless connector having a plurality of mating prongs extending radially from a flange rim; and a helix mount having a plurality of ceramic portion including a mount body, a mount flange, a mount connector, and a mount boss, wherein the mount body has a proximal mount face apposed to the distal flange end, the mourn flange extends radially outward from the mount body and helically about the longitudinal axis, and wherein the mount connector and the mount boss protrude proximally from the proximal mount face to form an annular channel receiving the flange such that the flange connector is between the mount connector and the mount boss.

19. The flange of claim 18, wherein a plurality of mating channels are defined between the plurality of mating prongs and the distal shoulder surface.

20. The flange of claim 18, wherein the plurality of mating prongs are evenly distributed about the longitudinal axis.

21. A method, comprising:
mounting, on a flange having a distal flange end and a flange channel extending along a longitudinal axis, a helix mount having a plurality of ceramic portions including a mount body, a mount flange, a mount connector, and a mount boss, wherein the mount body has a proximal mount face apposed to the distal flange end, the mount flange extends radially outward from the mount body and helically around the longitudinal axis, and wherein the mount connector and the mount boss protrude proximally from the proximal mount face to form an annular channel receiving the flange; and
mounting an electrode within a mount bore of the helix mount such that the electrode is disposed within the flange channel and the mount boss is between the flange and the electrode.

22. The method of claim 21 further comprising forming a joint between the flange, the helix mount, and the electrode, wherein the joint includes a filler metal.

23. The method of claim 21 further comprising mounting a fixation element on the mount flange of the helix mount, wherein the fixation element includes a helix revolving about the longitudinal axis.

24. The method of claim 21 further comprising mounting a proximal flange end of the flange on a housing having an electronics compartment containing an electronics assembly.

25. The method of claim 21, wherein the helix mount is entirely ceramic.

* * * * *